United States Patent [19]

Monty et al.

[11] 4,312,843

[45] Jan. 26, 1982

[54] DICALCIUM PHOSPHATE DIHYDRATE HAVING IMPROVED MONOFLUOROPHOSPHATE COMPATIBILITY AND PROCESS FOR THE PREPARATION THEREOF

[75] Inventors: Henri Monty, Mt. Kisco; Robert Querido, Spring Valley; Frances C. Benkwitt, Yonkers, all of N.Y.

[73] Assignee: Stauffer Chemical Company, Westport, Conn.

[21] Appl. No.: 106,637

[22] Filed: Dec. 26, 1979

[51] Int. Cl.$^3$ .............................................. C01B 25/32
[52] U.S. Cl. ................................ 423/267; 423/308; 423/309; 424/57
[58] Field of Search ............... 423/274, 309, 267, 308; 424/57

[56] References Cited

U.S. PATENT DOCUMENTS

| | | | |
|---|---|---|---|
| 2,018,410 | 10/1935 | McDonald et al. | 424/57 |
| 2,036,760 | 4/1936 | Knox, Jr. | 423/309 |
| 2,287,699 | 6/1942 | Moss et al. | 423/274 |
| 3,012,852 | 12/1961 | Nelson | 423/309 |
| 3,294,486 | 12/1966 | Cremer et al. | 423/309 |
| 4,193,973 | 3/1980 | Jarvis et al. | 423/308 |
| 4,244,931 | 1/1981 | Jarvis et al. | 423/311 |
| 4,247,526 | 1/1981 | Jarvis et al. | 423/308 |

OTHER PUBLICATIONS

Sienko et al., *Chemistry*, Second Edition, McGraw-Hill Book Company, Inc. (1961), p. 507.

*Primary Examiner*—O. R. Vertiz
*Assistant Examiner*—Wayne A. Langel
*Attorney, Agent, or Firm*—William C. Gerstenzang

[57] ABSTRACT

Dicalcium phosphate dihydrate compositions having improved monofluorophosphate compatibility are prepared by adding pyrophosphoric acid to the dicalcium phosphate reactor, terminating the reaction by which the dicalcium phosphate is formed at a pH ranging from 4.9 to 5.5 and blending the final product with a stabilizing agent.

9 Claims, No Drawings

DICALCIUM PHOSPHATE DIHYDRATE HAVING IMPROVED MONOFLUOROPHOSPHATE COMPATIBILITY AND PROCESS FOR THE PREPARATION THEREOF

BACKGROUND OF THE INVENTION

The present invention relates to dicalcium phosphate compositions having improved monofluorophosphate compatibility, and to a process for the preparation thereof.

Dicalcium phosphate has been used as a dental abrasive agent in toothpastes and powders for many years. This material is typically produced by first reacting a slaked lime slurry with phosphoric acid to form a dicalcium phosphate dihydrate precipitate, and then separating the dicalcium phosphate dihydrate precipitate from the mother liquor after which it is dried and milled to form the final product as a fine powder.

One serious problem which was initially encountered in the use of dicalcium phosphate dihydrate in toothpaste was the tendency of the dicalcium phosphate to "set-up" and become lumpy. When this occurs in toothpaste formulations, it makes it difficult to extrude the toothpaste from the tube in which it is usually packaged.

A second problem was encountered with the advent of the use of monofluorophosphate additives in toothpaste formulations. It was found that the monofluorophosphate components would react with the dicalcium phosphate whereby the monofluorophosphate component was converted from a water-soluble form to an insoluble form. Since the beneficial effect of monofluorophosphate additives in toothpaste are understood to be derived principally from the water-soluble form, it has become important to develop toothpaste formulations which permit an effective amount of monofluorophosphate component to remain in the water soluble state.

The term "monofluorophosphate-compatibility" has been used as a term-of-art to describe the tendency of such formulations to permit the monofluorophosphate component to remain in the water soluble state.

The monofluorophosphate compatibility of a particular formulation may be determined by a variety of methods. Preferably, the monofluorophosphate compatibility of a formulation may be determined by actually preparing the formulation, placing it in storage for a predetermined period of time under controlled conditions, and then determining the amount of water-soluble monofluorophosphate which remains in the formulation after having been stored under these conditions. Alternatively, a simulated formulation, such as the dicalcium phosphate dihydrate to be tested, glycerine and a known amount of a monofluorophosphate component, such as sodium monofluorophosphate can be "quick aged" by maintaining at an elevated temperature for one or more hours, and the amount of water-soluble monofluorophosphate remaining after such conditioning then determined. There are, of course, many other methods for measuring the relative monofluorophosphate compatibility of various samples of dicalcium phosphate dihydrate.

U.S. Pat. No. 2,287,699 teaches that dicalcium phosphate dihydrate may be stabilized by adding small amount of an alkali metal pyrophosphate to the mother liquor, at a controlled pH, during the preparation of the dicalcium phosphate. Specifically, it is taught that after precipitation of the dicalcium phosphate in the mother liquor, a small amount of alkali metal pyrophosphate should be added and the entire slurry then heated for a short period of time, while maintaining the pH of the mother liquor above 7.

Alternatively, the precipitate may be treated during the subsequent washing step.

It is also known to those skilled in the art that other forms of pyrophosphate can also be used to stabilize the dicalcium phosphate.

Another method for stabilizing dicalcium phosphate is disclosed in U.S. Pat. No. 2,018,410. This patent teaches that dicalcium phosphate can be stabilized by the addition thereto of a magnesium salt such as trimagnesium phosphate, magnesium sulfate, magnesium stearate, or dimagnesium phosphate.

It is known that at least some of these stabilizing agents also improve the monofluorophosphate compatibility of the dicalcium phosphate.

A complete solution to the problems presented by incompatibility between dicalcium phosphate dihydrate and monofluorophosphate additives in toothpastes however, has not yet been found, and the need for further improvements is well-recognized by the industry.

SUMMARY OF THE INVENTION

In accordance with the present invention there is now provided a process for preparing dicalcium phosphate dihydrate compositions which have improved monofluorophosphate compatibility. This process comprises the steps of:

(1) reacting a slaked lime slurry with phosphoric acid to form a monocalcium phosphate solution;

(2) adding to the solution additional amounts of the slurry and from about 0.1% to about 1.0% pyrophosphoric acid, by weight of dicalcium phosphate dihydrate to be formed, to form a dicalcium phosphate dihydrate slurry having a pH ranging from about 4.9 to about 5.5;

(3) separating the dicalcium phosphate dihydrate from the slurry; and (4) blending the dicalcium phosphate dihydrate with a stabilizing agent.

In a preferred embodiment, the monocalcium phosphate solution is formed and then additional slaked lime slurry is added to the monocalcium phosphate solution in an amount sufficient to form a dicalcium phosphate dihydrate slurry having a pH ranging from about 5.4 to about 5.9. Pyrophosphoric acid is then added in an amount sufficient to reduce the pH to from about 4.9 to about 5.5; provided however that the amount of pyrophosphoric acid so added is at least 0.1% by weight of dicalcium phosphate dihydrate to be produced. The process, in accordance with this preferred embodiment may therefore be defined as:

(1) reacting a slaked lime slurry with phosphoric acid to form a monocalcium phosphate solution;

(2) blending into the solution additional slaked lime slurry in an amount sufficient to form a dicalcium phosphate dihydrate slurry having a pH ranging from about 5.4 to about 5.9;

(3) blending into the dicalcium phosphate dihydrate slurry an amount of pyrophosphoric acid sufficient to reduce the pH of the slurry to from about 4.9 to about 5.5 provided, however, that the minimum amount of pyrophosphoric acid so added is at least 0.1% by weight of dicalcium phosphate dihydrate.

(4) separating the dicalcium phosphate dihydrate from the slurry.

DETAILED DESCRIPTION OF THE INVENTION

In preparing the dicalcium phosphate dihydrate composition of the present invention, the pyrophosphoric acid and lime slurry added in the second step may be added in any order, so long as the terminal pH of this step is within the specified limits.

The lime which is used in the practice of the present invention is the same type rotary kiln lime or shaft kiln lime as is used in conventional dicalcium phosphate processes.

The slaked lime slurry is prepared by mixing lime with either water or recycled mother liquor (i.e., that which remains after removal of the dicalcium phosphate dihydrate product from the final slurry), or both, in amounts of from about 100 to about 150 grams CaO/liter and at a temperature preferably ranging from about 70° C. to about 74° C. At higher concentrations the mixture will become a gelatinous mass which will be difficult to handle, while at concentrations below the range specified the process "payload" will be unnecessarily reduced.

The slaked lime slurry is then added to phosphoric acid to form a monocalcium phosphate solution.

The acid which is used is preferably a food grade phosphoric acid, preferably at an initial concentration of about 85%. Varying amounts of recycled mother liquor may also be added to the lime slurry and phosphoric acid, with the specific amount in each case being determined in accordance with the preferences of the individual practitioner. The compositional range of the monocalcium phosphate solution will be approximately as follows:

|  | Amount | |
| --- | --- | --- |
|  | High (Wt. %) | Low (Wt. %) |
| CaO | 4 | 2 |
| $P_2O_5$ | 22 | 12 |
| pH | 2 | 1 |

These ranges are set forth as examples of those which are typical, and are in no way intended to be limitations on the scope of the present invention. Those skilled in the art will understand that higher and lower amounts may also be used, provided that the reaction mixture meets the requirements of the practitioner.

When the lime slurry and phosphoric acid are brought together under the conditions specified above, a reaction will ensue and a monocalcium phosphate solution will be formed. The essential completion of the reaction will be indicated by a steady-state pH of from about 1.0 to about 2.0.

The preparation of the monocalcium phosphate solution can be carried out as a continuous, batch or semi-batch process.

Once the monocalcium phosphate solution has been formed, the pyrophosphoric acid and additional slaked lime are added to form the dicalcium phosphate dihydrate slurry. This reaction is exothermic and external cooling is required to control the reaction temperature. The reaction temperature should be controlled at or below about 45° C. At temperatures above about 45° C., anhydrous dicalcium phosphate crystals may be formed.

It is preferable to first add the additional slaked lime slurry to the monocalcium phosphate solution in an amount sufficient to form a slurry having a pH ranging from about 5.4 to about 5.9, although a pH of 5.7 is most preferred. Once the specified pH is achieved, on a steady-state basis, in this preferred embodiment, the pyrophosphoric acid is added in an amount sufficient to reduce the pH to a pH ranging from about 4.9 to about 5.5, although a pH of from about 5.2 to about 5.4 is preferred and a pH of 5.3 is most preferred. The minimum amount of pyrophosphoric acid which should be added is about 0.1% by weight of dicalcium phosphate dihydrate to be prepared while the maximum required should be about 1.0%.

Although it is preferable to add the pyrophosphoric acid and slaked lime slurry to the monocalcium phosphate solution in the sequence just described, it is within the scope of the invention to add these two ingredients in other than that sequence. It is, however, important that the terminal pH, after both of these ingredients are added, ranges from about 4.9 to about 5.5 and preferably, that it be about 5.3.

It is, for example, within the scope of the present invention to add the pyrophosphoric acid before the additional slaked lime slurry, or together with the slaked lime slurry. The amount of pyrophosphoric acid added should range from about 0.1% to about 1.0%, by weight of dicalcium phosphate dihydrate to be produced, and preferably, from about 0.3% to about 0.4%.

Once the dicalcium phosphate dihydrate slurry has been formed as described above, the dicalcium phosphate dihydrate product is separated from the mother liquor. The mother liquor may then be recycled to the beginning of the process, or discarded.

The separation of the dicalcium phosphate dihydrate from the slurry can be accomplished by any of several conventional techniques. These techniques include, but are not limited to, decantation, centrifugation, filtration and the like, although decantation is preferred because of its simplicity.

Once the dicalcium phosphate dihydrate is separated from the slurry, it can be dried, milled and mixed with a stabilizer.

The stabilizers which are added to dicalcium phosphate dihydrate are intended to prevent the "caking" and "lumping" which occurs in unstabilized dicalcium phosphate dihydrate as a result of dehydration. There are many stabilizers known to be useful for this purpose. These include, but are not limited to dimagnesium phosphate, trimagnesium phosphate, magnesium stearate and magnesium sulfate. The amount of stabilizer added ranges from about 0.5% to about 5.0% by weight of dicalcium phosphate dihydrate. Preferred stabilizers for use in the practice of the present invention are dimagnesium phosphate trihydrate, trimagnesium phosphate octahydrate, and mixtures thereof.

Surprisingly and unexpectedly it has been found that when dimagnesium phosphate trihydrate and/or trimagnesium phosphate octahydrate are added to the dicalcium phosphate prepared in accordance with the present invention, a substantial improvement in monofluorophosphate compatibility is achieved. Dimagnesium phosphate trihydrate is particularly effective in this regard. This improvement is substantially greater than that achieved by adding either of these compounds to dicalcium phosphate dihydrate prepared by conventional techniques.

It is preferred to add the stabilizer to the dicalcium phosphate dihydrate by dry-blending these two components after the dicalcium phosphate dihydrate has been dried or after it has been dried and milled. It is, however, within the scope of the invention to add the stabilizer to the product slurry before separating the dicalcium phosphate dihydrate therefrom; or to the "wet" dicalcium phosphate dihydrate prior to drying and milling.

In order that the present invention be more fully understood, the following examples are given by way of illustration. No specific details or enumerations contained therein should be construed as a limitation on the present invention except insofar as they appear in the appended claims.

EXAMPLE 1

A slaked lime slurry prepared from rotary kiln lime (about 134 grams CaO/liter) was added, with stirring, to 85% food-grade phosphoric acid and recycled mother liquor to form a clear solution of monocalcium phosphate having about 15.5% $P_2O_5$, 3.3% CaO and a pH of 1.6.

Additional slaked lime slurry was then added, with stirring, to the monocalcium phosphate solution until the pH reached about 5.0, whereupon about 0.34 parts of total mixture of pyrophosphoric acid by weight was added. Slaked lime slurry addition was resumed and continued until the pH reached about 6.2. External cooling was applied to maintain the temperature of the mixture at about 45° C. during these additions.

The resulting dicalcium phosphate dihydrate slurry was permitted to stand without stirring for about 30 minutes, after which the mother liquor was removed by decantation. The dicalcium phosphate dihydrate product was then dried and milled.

A portion of the dicalcium phosphate dihydrate was then used to prepare a standard toothpaste formulation which also included sodium monofluorophosphate in an amount equivalent to 1000 ppm fluoride ion.

A second portion of the dicalcium phosphate dihydrate was blended with 2 percent by weight of total of trimagnesium phosphate octahydrate; a third portion with 1 percent dimagnesium phosphate trihydrate; a fourth portion with 3 percent dimagnesium phosphate trihydrate and a fifth with 5 percent dimagnesium phosphate trihydrate.

Each of these portions was then used to prepare toothpaste formulations similar to that prepared with the first portion.

Each formulation was then aged for three weeks at 49° C., after which the amount of water soluble monofluorophosphate remaining was determined, with the following results:

| Stabilizer | Amount % | Available Fluoride, as total water-soluble Fluoride ($F^-$), after 3-weeks at 49° C. (ppm) |
| --- | --- | --- |
| None | — | 340 |
| Trimagnesium phosphate octahydrate | 2 | 470 |
| Dimagnesium phosphate trihydrate | 1 | 540 |
| Dimagnesium phosphate trihydrate | 3 | 530 |
| Dimagnesium phosphate trihydrate | 5 | 530 |

This shows that the addition of trimagnesium phosphate octahydrate or dimagnesium phosphate trihydrate to the dicalcium phosphate dihydrate used in toothpaste formulations results in improved monofluorophosphate compatibility in prior art dicalcium phosphate dihydrate compositions.

EXAMPLE 2

A quantity of dicalcium phosphate dihydrate was prepared as in Example 1, except that the final slaked lime slurry addition was terminated at a pH of 5.3. Portions of this dicalcium phosphate dihydrate were then used to prepare toothpaste formulations which were then aged and tested for fluoride compatibility as in Example 1, with the following results:

| Stabilizer | Amount % | Available Fluoride, as total water-soluble Fluoride ($F^-$), after 3-weeks at 49° C. (ppm) |
| --- | --- | --- |
| None | — | 420 |
| Trimagnesium phosphate octahydrate | 2 | 690 |
| Dimagnesium phosphate trihydrate | 1 | 900, 840 |

This example shows that dicalcium phosphate dihydrate prepared in accordance with the process of the present invention has a higher monofluorophosphate compatibility than that prepared by the prior art methods (Example 1). In addition, the dicalcium phosphate dihydrate prepared according to the process of the present invention provides unexpectedly superior monofluorophosphate compatibility when combined with stabilizers.

EXAMPLE 3

A quantity of dicalcium phosphate dihydrate was prepared as in Examples 1 and 2 except that the slaked lime slurry was added to the monocalcium phosphate solution until the pH reached about 5.6 and then pyrophosphoric acid was added until the pH was reduced to about 5.3; no further slaked lime slurry was added.

Portions of this dicalcium phosphate dihydrate were then blended with stabilizers and used to prepare toothpaste formulations which were aged and tested as in the previous examples, with the following results:

| Stabilizer | Amount % | Available Fluoride, as total water-soluble Fluoride ($F^-$), after 3-weeks at 49° C. (ppm) |
| --- | --- | --- |
| None | — | — |
| Trimagnesium phosphate octahydrate | 2 | 680 |
| Dimagnesium phosphate trihydrate | 1 | 800 |
| Dimagnesium phosphate trihydrate | 3 | 820 |

-continued

| Stabilizer | Amount % | Available Fluoride, as total water-soluble Fluoride ($F^-$), after 3-weeks at 49° C. (ppm) |
|---|---|---|
| Dimagnesium phosphate trihydrate | 5 | 820 |

This shows that the preferred embodiment of the process of the present invention produces dicalcium phosphate dihydrate having a higher monofluorophosphate compatibility than the prior art processes.

We claim:

1. A process for preparing dicalcium phosphate dihydrate compositions having improved monofluorophosphate compatibility which comprises the steps of:
   (a) reacting a slaked lime slurry with phosphoric acid to form a monocalcium phosphate solution;
   (b) adding to said solution additional amounts of said lime slurry and from about 0.1% to about 1.0% pyrophosphoric acid, by weight of dicalcium phosphate dihydrate to be formed, to form a dicalcium phosphate dihydrate slurry having a pH ranging from about 4.9 to about 5.5;
   (c) separating the dicalcium phosphate dihydrate from said slurry; and
   (d) blending said dicalcium phosphate dihydrate with a stabilizing agent.

2. The process of claim 1 wherein said stabilizing agent is added in an amount ranging from about 0.5% to about 5% by weight of dicalcium phosphate dihydrate and is dimagnesium phosphate, trimagnesium phosphate or mixtures thereof.

3. The process of claim 2 wherein said pH is about 5.3.

4. A process for preparing dicalcium phosphate dihydrate compositions having improved monofluorophosphate compatibility which comprises the steps of:
   (a) reacting a slaked lime slurry with phosphoric acid to form a monocalcium phosphate solution;
   (b) blending into said solution additional slaked lime slurry in an amount sufficient to form a dicalcium phosphate dihydrate slurry having a pH ranging from about 5.4 to about 5.9;
   (c) blending into said dicalcium phosphate dihydrate slurry an amount of pyrophosphoric acid sufficient to reduce the pH of said slurry to from about 4.9 to about 5.5 provided, however, that the minimum amount of pyrophosphoric acid so added is at least 0.1% by weight of dicalcium phosphate dihydrate;
   (d) separating said dicalcium phosphate dihydrate from said slurry; and
   (e) blending said dicalcium phosphate dihydrate with from about 0.5% to about 5% by weight of the dicalcium phosphate dihydrate of dimagnesium phosphate, trimagnesium phosphate or mixtures thereof.

5. The process of claim 4 wherein said pH in step "b" is 5.7.

6. The process of claim 5 wherein said pH of step "c" is 5.3.

7. The process of claim 6 wherein said dicalcium phosphate dihydrate is blended with trimagnesium phosphate.

8. A dicalcium phosphate dihydrate composition having an improved monofluorophosphate compatibility comprising a mixture of a stabilizing agent with a dicalcium phosphate dihydrate product prepared by the steps of:
   (a) reacting a slaked lime slurry with phosphoric acid to form a monocalcium phosphate solution;
   (b) adding to the solution additional amounts of the slurry and from about 0.1% to about 1.0% pyrophosphoric acid, by weight of dicalcium phosphate dihydrate to be formed, to form a dicalcium phosphate dihydrate slurry having a pH ranging from about 4.9 to about 5.5; and
   (c) separating the dicalcium phosphate dihydrate from the slurry.

9. The composition of claim 8 wherein said stabilizer is trimagnesium phosphate, dimagnesium phosphate or a mixture thereof and said pH is 5.3.

* * * * *